United States Patent
Owen et al.

(10) Patent No.: US 7,513,127 B2
(45) Date of Patent: Apr. 7, 2009

(54) ULTRA-LOW TEMPERATURE STORAGE SYSTEM

(75) Inventors: Stephen Owen, Cambridge (GB); Justin Michael Owen, Hertfordshire (GB)

(73) Assignee: The Automation Partnership, (Cambridge) Limited, Hertfordshire (GB)

( * ) Notice: Subject to any disclaimer, the term of this patent is extended or adjusted under 35 U.S.C. 154(b) by 0 days.

(21) Appl. No.: 11/224,327

(22) Filed: Sep. 13, 2005

(65) Prior Publication Data

US 2006/0053825 A1 Mar. 16, 2006

(30) Foreign Application Priority Data

Sep. 14, 2004 (EP) ................................. 04255545

(51) Int. Cl.
*F25D 25/02* (2006.01)
*F25D 11/02* (2006.01)

(52) U.S. Cl. .............................. 62/382; 62/441; 422/65; 436/47

(58) Field of Classification Search .................. 62/48.3, 62/302, 371, 378, 441; 422/63, 65, 67; 436/47, 436/48

See application file for complete search history.

(56) References Cited

U.S. PATENT DOCUMENTS

| | | | | |
|---|---|---|---|---|
| 6,059,196 A | * | 5/2000 | Miyazaki et al. | 236/44 A |
| 6,253,568 B1 | * | 7/2001 | Peffley | 62/441 |
| 6,468,800 B1 | * | 10/2002 | Stylli et al. | 436/43 |
| 6,472,218 B1 | * | 10/2002 | Stylli et al. | 436/48 |
| 6,560,973 B2 | * | 5/2003 | Jones et al. | 62/60 |
| 6,685,884 B2 | * | 2/2004 | Stylli et al. | 422/63 |
| 6,817,208 B2 | * | 11/2004 | Choi et al. | 62/408 |
| 6,974,294 B2 | * | 12/2005 | Pressman et al. | 414/331.03 |
| 6,979,425 B1 | * | 12/2005 | Ganz et al. | 422/100 |
| 2002/0012611 A1 | * | 1/2002 | Stylli et al. | 422/65 |

\* cited by examiner

*Primary Examiner*—Mohammad M. Ali

(57) ABSTRACT

A system 10 for storing and processing a plurality of biological or chemical samples at ultra-low temperatures is provided. The system 10 comprises a plurality of ultra-low temperature storage locations 30; an enclosed pathway 35 adjacent the storage locations 30; and a manipulator module 60 disposed within the pathway 35 for conveying vessels 33 along the pathway 35 between the storage locations 30 in the system 10. Each of the storage locations being accessed through an insulated access panel 36 on the side of the storage location 30, the panel 36 being configured to close the storage location 30 from the pathway 35.

19 Claims, 10 Drawing Sheets

ULTRA-LOW TEMPERATURE STORAGE SYSTEM

The present invention relates to a system for storing and processing a plurality of biological or chemical samples at ultra-low temperatures.

Drug discovery, within the context of the modern pharmaceutical industry, relies heavily on the storage and retrieval of a large number of samples for a variety of experiments or assays. Some of these samples may be taken from patients who are participating in clinical trials. Large pharmaceutical companies may run many clinical trials a year with thousands of patients per trial. Several samples may be stored from each patient. There is a need to provide suitable storage for the very large numbers of samples produced during such trails for other processes. Manual storage and retrieval from such a large store is problematic and prone to human error. Automated systems are preferred when dealing with upwards from tens of thousands of samples. The samples may be required to be stored for many years and should be capable of being easily extracted and used as a resource from which further experiments can be performed in different areas of research and development. It is therefore necessary in the context of drug discovery, and other similar pharmaceutical work, that samples should be stored in the optimum temperature and humidity environment so that they remain in pristine condition over long time periods and also that they should be quickly and reliably identifiable. This is a considerable technical challenge as laboratories may require to store millions of samples.

The storage temperature is dependent upon the type and stability of the sample to be stored, the length of time that the sample needs to be stored and the acceptable quality of the sample after a prolonged length of storage. Scientific opinion varies regarding the optimum storage temperature but it is generally accepted that sample degradation is reduced with lower storage temperatures. Organic compounds, which generally comprise small molecules, may be stored in their dry or powdered form at room temperature, whereas when dissolved in an organic compound such as DMSO lower storage temperatures such as 4° C. or even −20° C. may be preferred. More complex molecules such as DNA are preferably stored at −20° C. whilst even lower temperatures such as −80° C. are suggested for RNA, proteins and some other biological products. Storage temperatures below −132° C. (the glass transition temperature of water) may be recommended when cells are stored and cell viability is desired after thawing. Temperatures in the region of −80° C. are hereinafter referred to as ultra-low temperatures. The exact temperature may depend on the type of refrigerant and may be, for example −73° C. At these ultra-low temperatures greater engineering challenges are encountered as the physical properties of materials change with temperature, for example many materials become brittle at ultra-low temperatures.

In order to utilise the sample store efficiently it is vital that samples can easily be located and removed from the store. However, at the low temperatures (below freezing) at which these samples are stored any access to the external environment can result in temperature changes in some areas of the store and also the ingress of water vapour which, in turn, condenses to form ice that may contaminate samples or settle on mechanical equipment and prevent it from working properly. It is therefore advantageous to minimise the contact between the low temperature area and the external environment, (room temperature and humidity). This is particularly so at ultra low temperatures.

Furthermore, at ultra-low temperatures problems arise as a result of the fact that the physical properties of the materials used within the store are temperature dependent. This means that standard robots that are used to manipulate samples in stores that operate at −20° C. and above cannot work in the ultra-low temperature regime as some of the materials become brittle. This, in turn, leads to considerable technical problems in the use of standard robotics within an ultra-low temperature store.

According to the present invention there is therefore provided a system for storing and processing a plurality of biological or chemical samples at ultra-low temperatures, the system comprising:

a plurality of ultra-low temperature storage locations;

an enclosed pathway adjacent the storage locations;

a manipulator module disposed within the pathway for conveying vessels along the pathway between the storage locations in the system;

each of the storage locations being accessed through an insulated access panel on the side of the storage location, the panel being configured to close the storage location from the pathway.

The partition of the system into ultra-low temperature storage locations and an isolated pathway that is maintained well below room temperature but above ultra-low temperature overcomes the problem encountered in known systems whereby either the samples are exposed to comparatively high temperatures as they are moved into and out of the system or considerable technical expertise and expense is required in order to provide a robot capable of functioning at ultra-low temperatures.

The system preferably further comprises at least one module for housing the storage locations.

This modular construction is advantageous because it improves the long-term stability of samples stored and, in the unlikely event of a failure in the cooling mechanism, a limited number of samples are affected.

Furthermore, according to the present invention there is provided an enclosure for storing and processing a plurality of biological or chemical samples at ultra-low temperatures, the enclosure comprising:

walls to close the enclosure;

a plurality of modules defined by walls wherein each module comprises a plurality of compartments and is maintained, in use, at about −80° C.;

a pathway maintained, in use, at about and situated adjacent the modules;

wherein walls of the enclosure are separated from the walls of the modules.

The performance and longevity of the enclosure is key to the performance of the system, especially with regard to its long-term viability. The enclosure must provide the required level of thermal insulation and it must also retard the ingress of moisture to prevent icing.

When dealing with ultra-low temperatures, a single skinned enclosure construction is not the best approach, because panel stresses that occur due to differential contraction through the structure can cause the sealing between the panel joins to fail during the life of the store. Such failures would be difficult to identify and remedy without compromising the samples.

Alternative examples of the present invention will now be described with reference to the drawings in which.

Figure 1:
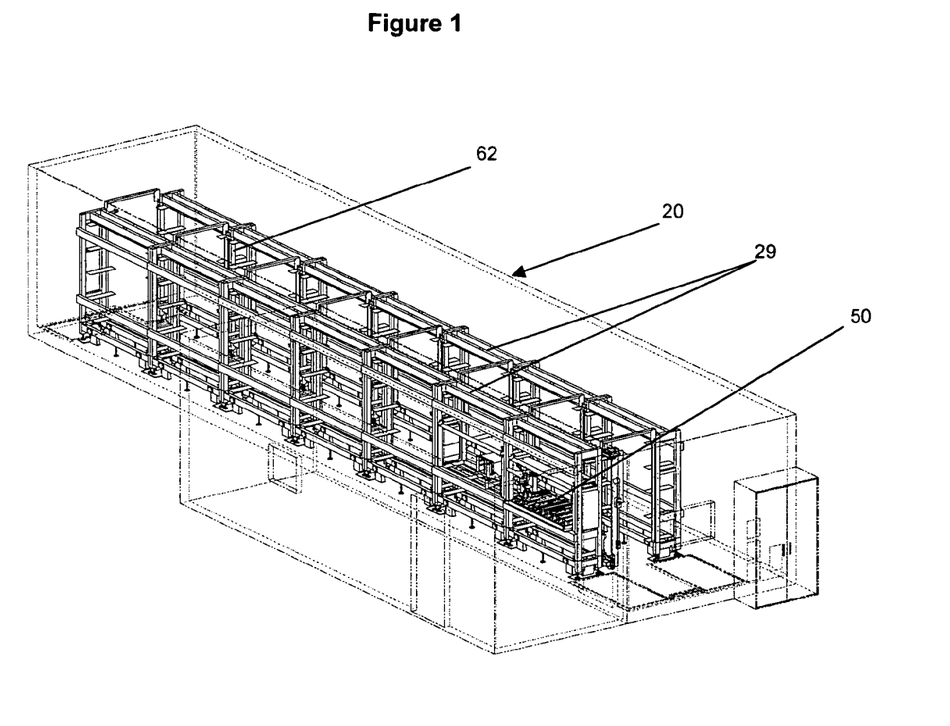
FIG. 1 is an isometric view of a system according to the present invention.
Figure 2:
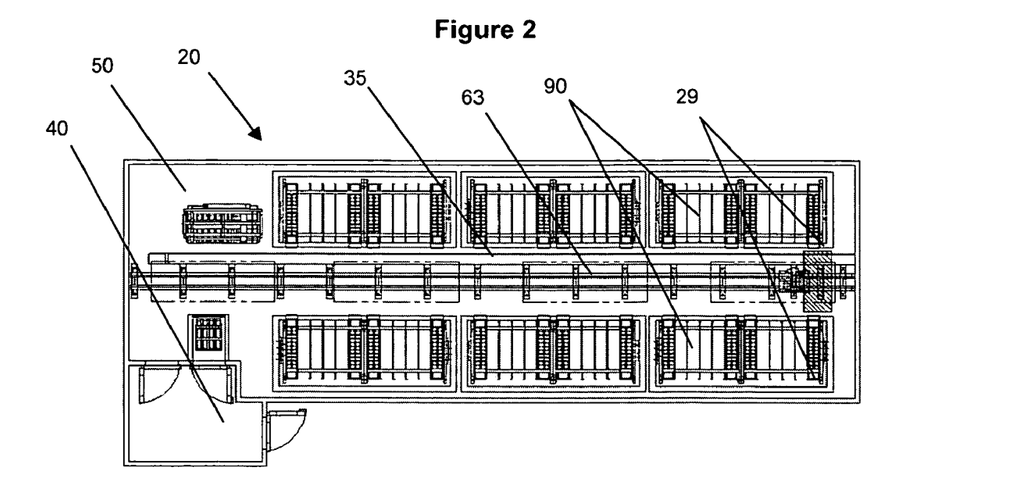
FIG. 2 shows a plan view of a second example of a system according to the present invention.

The system 10 of the present invention, as illustrated in FIGS. 1 and 2, comprises an enclosure 20, storage racking 29, a corridor 35, a loading buffer 40, a vessel picking station 50 and a transfer robot or manipulator module 60. Each enclosure 20 may be provided with more than one transfer robot 60. Although only one robot 60 is shown in FIG. 1, more than one can be used. The corridor 35 is provided with a parking area 37 where one or more of the robots 60 may remain when not in use.

The enclosure 20 is in the form of an elongate cuboid. The storage racking 29 is provided along the two major walls of the enclosure 20 in a plurality of modules 90. Each module 90 is a self-contained unit, insulated from the corridor 35 and the other modules 90. Furthermore, scaling the system to fit the needs of different user is easier with a modular system. When a system 10 is installed a further module 90, additional to the expected storage requirements of the system, may be included in order to create a given level of redundancy in the system. The robot 60 operates in the corridor 35 between the modules 90 that lie adjacent the walls of the enclosure 20. In a second example of the present invention (not shown) only one set of modules 90 containing storage racking 29 is provided adjacent the corridor 35.

Each module is divided into a number of compartments 31 each of which is designed to house a drawer 34 or a tray 32. A drawer 34 consists of a lower surface on which a plurality of sample vessels 33 may be stored; side portions that interface, in use, with the module 90 and an integral access panel 36. In contrast a tray 32 comprises only a surface on which a plurality of sample vessels 33 may be stored and means for retaining the tray 32 in the compartment 31 of the module 90. The lower surface of the drawer 34 or tray 32 may support a plurality of vessels 33 which may be well known SBS format microtitre plates (not shown); tubes (not shown) or racks 33a. The drawers 34, trays 32 and sample vessels 33 provide a plurality of storage locations 30. The modules 90 are provided with a plurality of vertical walls each of which comprises a number of grooves with which the drawers 34 interface, in use.

In use, the interior of each module 90 is maintained at ultra-low temperature, i.e. preferably in the region of −80° C. and the corridor 35 is maintained at around −20° C.

Figure 3:
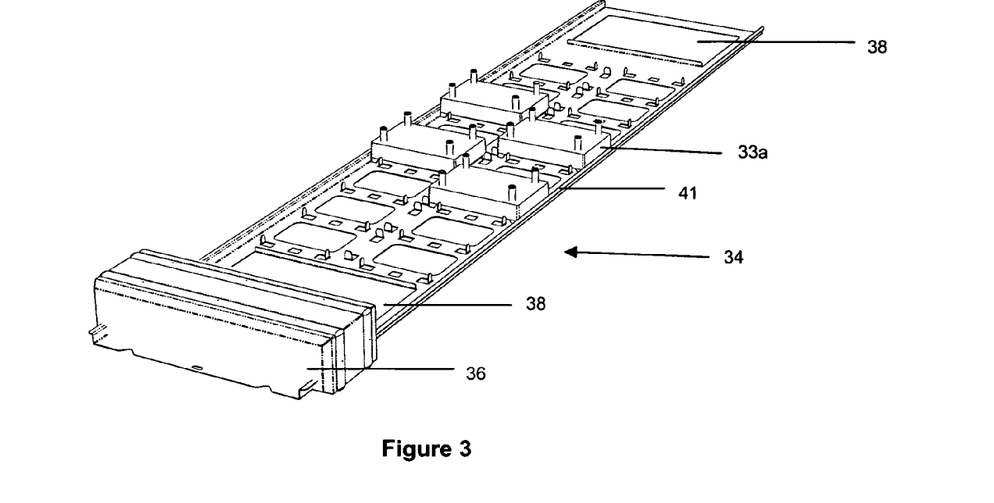
FIG. 3 is a side perspective view of a drawer.
Figure 8:
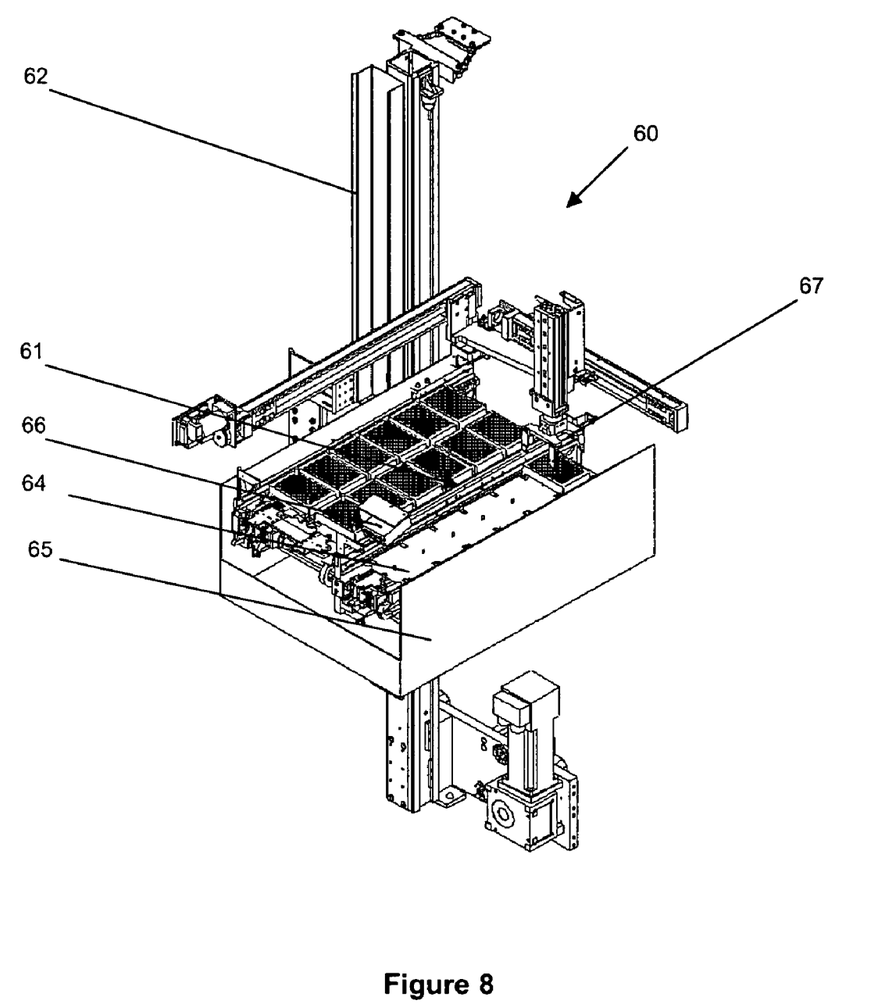
FIGS. 8 and 9 show the manipulator module with and without a protective surround.
Figure 9:
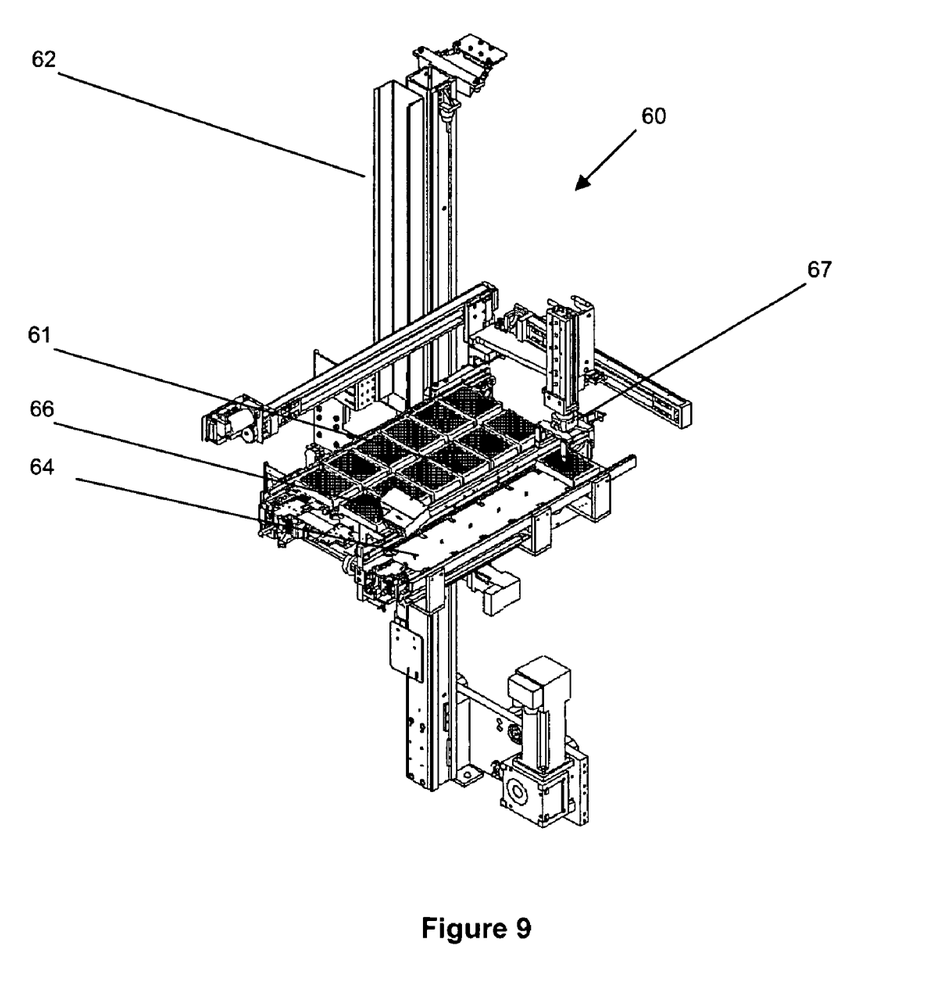

The storage racking 29 is fabricated entirely from grade 304 austenitic stainless steel because the very low temperatures within the modules 90 are unsuitable for most modern low carbon steels which only have sufficient fracture toughness to ensure that failure does not occur down to −40° C. In order to enable the removal of the vessels 33, access is obtained by sliding the drawer 34 sufficiently into the corridor 35 that the vessel 33 to be accessed emerges from the module 90, as shown in FIG. 3. Gripping means 67 (see FIGS. 8 and 9) are provided on the robot 60 to transfer any type of vessel 33 from the drawer 34. Furthermore, if individual tubes are used without racks then the lower surface of the drawer 34 is provided with a matrix aperture suitable for retaining individual tubes.

Figure 4:
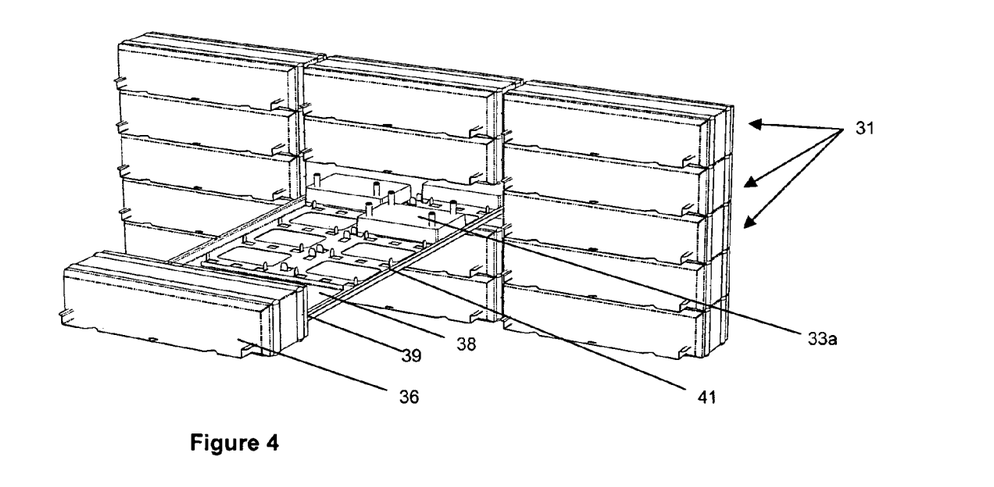
FIG. 4 shows the drawer being inserted into the system of the present invention.

FIG. 4 is a schematic of one of the many drawers 34 that can be stored in each module 90. The drawer 34 is fabricated from an aluminium sheet, punched and folded for optimum stiffness and low weight. Two SBS format racks 33a, each containing a plurality of tubes, can be slotted onto the lower surface of the drawer 34. At the front and rear of each drawer 34 or tray 32 are apertures 38 that, when all of the compartments 31 within each module 90 are occupied, provide a chimney effect, helping to move air from the bottom of the module to the top. This helps to isolate the contents of the sample vessels 33 from heat ingress through the drawer front and rear of the module 90. Folded tabs 41 locate the drawers 34 in the module 90 and folds along the edges of the drawer 34 and the apertures 38 provide longitudinal and transverse stiffness.

The front face of each of the compartments 31 is each provided with an insulated access panel 36 that, in use, forms a seal between the corridor 35 and the interior of the module 90. Where the compartment 31 is occupied by a drawer 34 the access panel 36 is formed as an integral part of the front face of the drawer 34. If a tray 32 is used in the compartment 31 a separate insulated door (not shown) is provided. In this embodiment the access panel takes the form of a pivotable, removable or slidable door portion that is actuated by the robot in order to allow the tray to be drawn from the compartment 31.

The access panel 36 is made from low-density polyurethane foam and is moulded onto the drawer 34. Such foam has a very low thermal conductivity and has sufficient density and surface hardness for the intended usage. The seal 39 is made from a very low temperature silicone compound which remains flexible at −80° C. The compartments 31, drawers 34 and their respective access panels 36 may be provided in a number of different sizes in order to accommodate vessels 33 of different sizes. It will be apparent to the man skilled in the art that larger or smaller vessels 33 may be used dependent upon the size of sample required and the number of samples that require storage. The provision of an access panel 36 that is an integral part of the drawer 31 is advantageous because it reduces the number of actions required by the robot in order to gain access to a sample vessel 33.

Figure 5A:
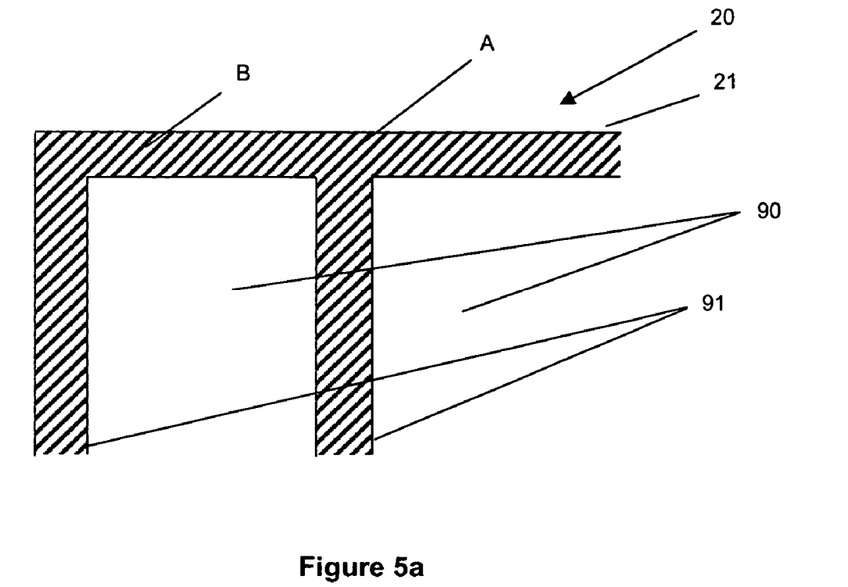
FIGS. 5a and 5b show plan views of two different module constructions.
Figure 5B:
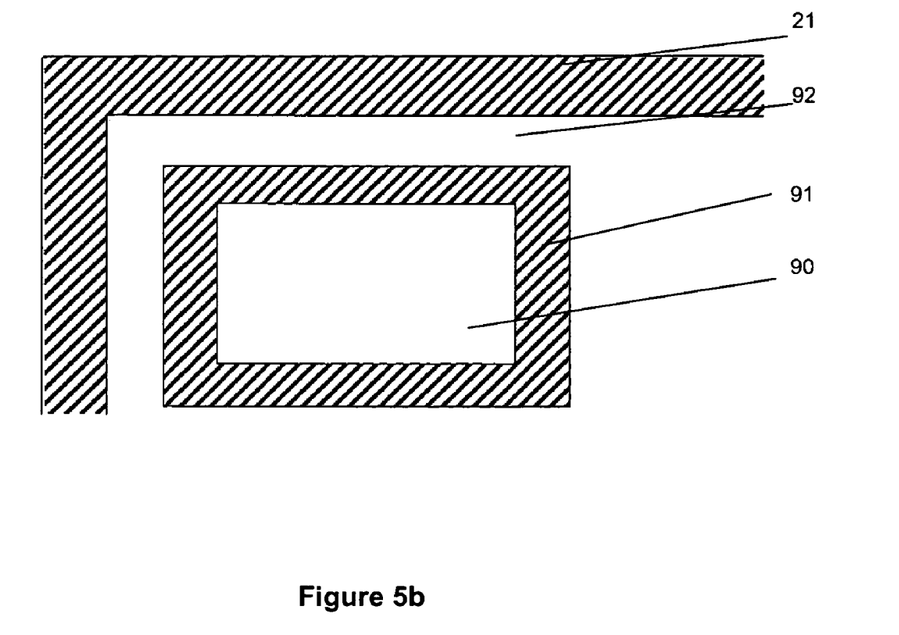

FIGS. 5a and 5b show, schematically, the differences between the single skinned enclosure (FIG. 5a) and the preferred construction called hereinafter, a "box-within-a-box" construction, shown in FIG. 5b.

Referring first to FIG. 5a, it is the case that severe stresses may build up at a point A where the panel walls have three different temperature zones on different faces. Furthermore, at point B, which has the maximum temperature differential across a single boundary, any joint failure will allow moisture to enter the module 90. This can lead to frosting which can compromise the integrity of the samples.

Referring to FIG. 5b, each module 90 is enclosed by a high integrity wall 91. This wall 91 is separated, by a layer 92 of air, from the wall 21 of the enclosure 20, which acts as an additional insulator. This minimises the change in temperature across any one wall.

Figure 6:
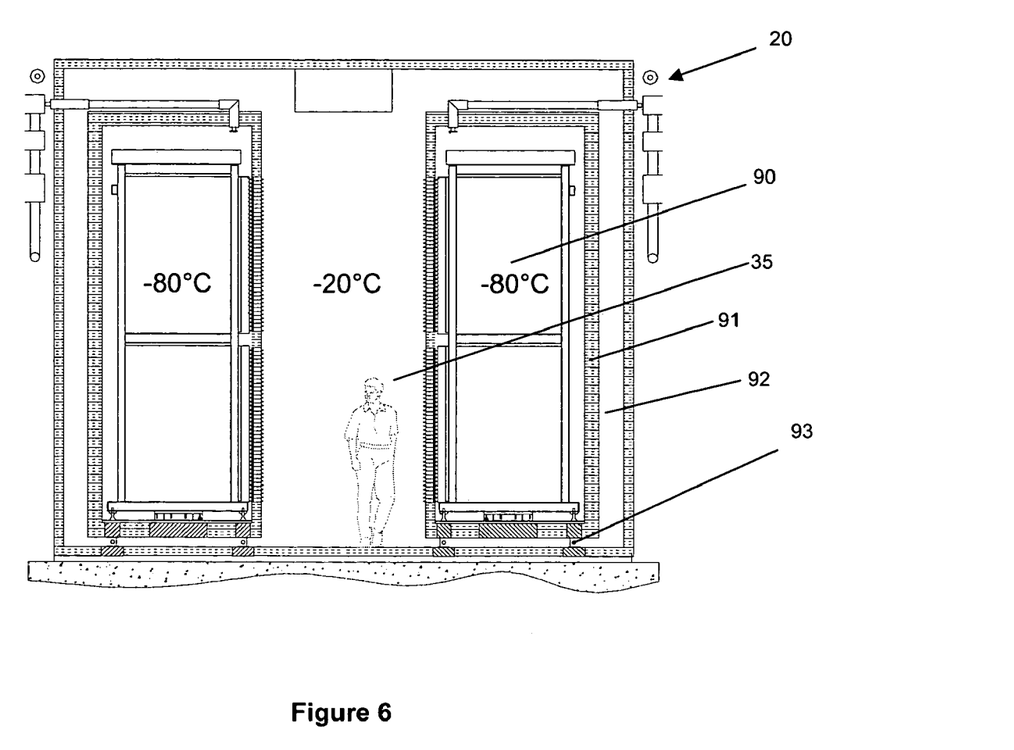
FIG. 6 shows a cross section through the system of the present invention.

FIG. 6 shows a cross section of the system 10 including modules 90 with construction as shown in FIG. 5b. The layer 92 of air extends around all faces of the module including above and below the module 90. In order to provide the layer 92 of air beneath the module 90, the module is mounted on load-bearing support blocks 93. The modules are typically approximately 5 m high.

The provision of the layer 92 of air is advantageous not only for the integrity of the samples and reduction in temperature gradient across the walls 21, 91. It also helps to prevent frost heave in the ground below the system 10. Frost heave occurs when the ground under a cold store freezes and expands causing damage to the building floor and the cold room itself.

Trace heating, either in the form of prefabricated mats or resistance wire embedded in screed, is the most common method of preventing frost heave. However the repair or replacement of such systems without decommissioning the store is not possible and there is little evidence to suggest that they will last for 25 years. Multiple redundant elements could be employed but are an expensive solution.

The system 10 uses natural ventilation as a means of preventing frost heave. Load bearing ventilation blocks may be sandwiched between the building floor and the underside of the system 10 in order to break the conductive heat transfer path. These blocks are vertically aligned with the support blocks 93 that separate the module 90 from the wall of the enclosure 20 thereby ensuring the structural integrity of the system 10. A ventilated floor is intrinsically more reliable than trace heating.

Within the enclosure 20 there is provided a loading buffer 40. This area enables samples to be introduced into the system 10 in a controlled environment without unduly affecting the temperature of the storage racking 29. The loading buffer is provided with a system to reduce the humidity of the air in order to avoid the introduction of moisture to the storage area 30 and subsequent problems with icing. The samples are presented to the store frozen and the loading buffer 40 executes a −70° C. dewpoint purge cycle before the samples are moved into the corridor 35 and subsequently into a module 90. The enclosure 20 operates with a maximum dewpoint of −40° C. The loading buffer 40 may be maintained at −20° C. or −80° C. depending on requirements. Whether the loading buffer is maintained at −20° C. or −80° C. may depend, for example, on, amongst other things, how long trays 32 or racks 33a are held in the buffer 40 prior to inclusion in a storage rack 30 or how long they are required to remain in the buffer before removal from the system. Some samples may need to be cooled immediately to −80° C.

In this example the enclosure 20 is also provided with a vessel picking station 50. This station 50 is provided with a number of robotic picking and placing machines that allow a high throughput of samples. The vessel picking station 50 is maintained at −20° C.

The robot 60 is free to move along the entire length of corridor 35, see FIG. 2, and move samples from compartments 31 to the vessel picking station 50. The robot 60 includes a mast 62, which allows it to move in the vertical plane in order to access trays 32 or drawers 34 in different parts of the storage racking 29. The mast 62 is, in turn, mounted on rails 63 that allow the mast 62 and the robot 60 to move along the corridor 35 to access compartments 31 in different locations within the storage racking 29.

Figure 7:
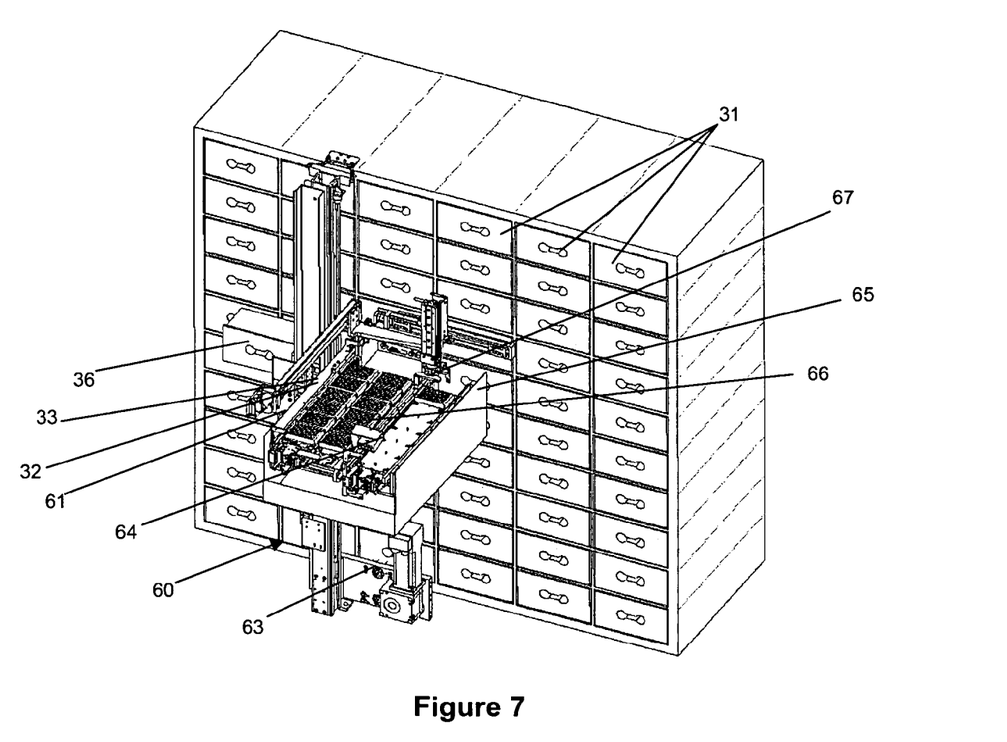
FIG. 7 shows the manipulator module accessing a compartment within the system of the present invention.

The robot 60 is also provided with a transfer portion 61, which comprises a flat bed onto which an SBS format rack 33a may be transferred, in use, see FIG. 7. The transfer portion is protected on three sides by a surround 65, which prevents the cold air surrounding the vessels 33 from flowing away. The surround 65 therefore helps to maintain the temperature of the samples whilst the vessels 33 are not in the racking 30. Mounted above the transfer portion 61 on the mast 62 there is a code reader 66 which may read a 2D (dot) code or a bar code that has been applied to any vessel 33 removed from the rack 33a. The transfer robot 60 is controlled by a velocity ramp servo controller in order to provide a smooth movement.

Mounted alongside the transfer portion 61, within the surround 65 there is a dummy tray 64. During the operation of the robot 60 an access door is opened on one of the compartments in the storage racking and the tray is pulled out. In an alternative example, which is considered to be preferable, the drawer 34 is pulled from the compartment 31 using the access panel 36 mounted thereon. Selected contents of the tray 32, whether they are individual tubes, plates or SBS format racks 37 can be removed from the tray 32 or drawer 34 and placed into the dummy tray 64. The contents of the dummy tray 64 can then be transferred to the vessel picking station 50. In this station 50 the required samples are extracted from the vessels 33 before the remaining contents are returned to the tray 32. The open configuration of the transfer portion 61 and dummy tray 64 allows easy access to the vessels 33 that have been transferred from the tray 32 or drawer 34. The temperature is not adversely affected by the open configuration of the transfer portion 61 and dummy tray 64 as the cold air tends to settle around the open tray insulating the contents.

In a further example of the present invention, not shown in the figures, individual tubes can be picked directly from the SBS format racks 37 by the gripping means 67 mounted on the mast 62. This configuration allows individual tubes to be picked from racks that remain within their respective trays or drawers and therefore do not have to be removed to the picking station thereby minimising the time when the samples contained in the vessels 33 are exposed to warmer air than that in the module 90. This example of the present invention is preferred in cases where only one or two samples are required from each individual rack 37.

The maintenance of the environmental conditions is essential to ensure sample quality. The system, shown schematically in block diagram form in FIG. 10, includes a 100% dual redundant mechanical refrigeration using −80° C. cascade chillers 80 and air handling comprising coolers 70 for the −80° C. modules 90, containing the storage racking 29, and separate −20° C. climate control system 85 for the corridor 35.

Figure 10:
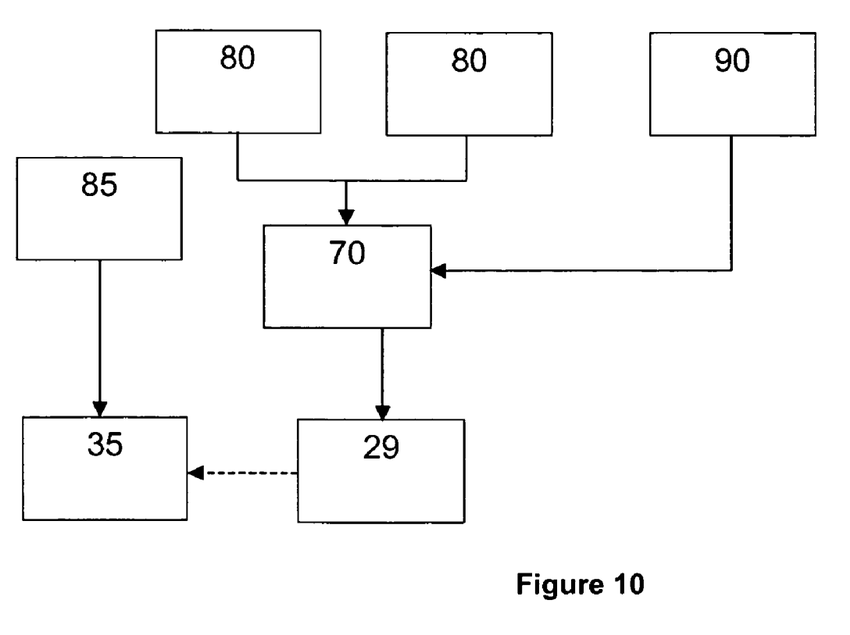
FIG. 10 is a schematic of the refrigeration system.

Dry air is blown into the modules 90 or pathway 35 through the coolers 70, this extremely low humidity air is necessary to prevent condensation or frosting anywhere within the store enclosure. Some air will flow from the storage racking 29 to the corridor 35 (indicated by the dashed line arrow between the racking 30 and the corridor 35) and this will keep the humidity in the corridor 35 low and also provide some cooling. This may be sufficient and no extra cooling may be necessary. Indeed, if the robot 60 in the corridor 35 has a particularly low duty cycle then it may be necessary for the climate control system 85 to heat the air that it introduces into the corridor to ensure the effective working of the tray transfer robot 60. Alternatively if the duty cycle of the robot 60 is high and it generates a lot of heat then the climate control system 85 will need to reduce the temperature of the air that it introduces into the corridor 35.

A mechanical refrigeration system can be used because the running costs are significantly lower than the corresponding costs for a system cooled by a liquid nitrogen heat exchanger, however in order to deal with the possibility of failure of both mechanical cooling systems, the store incorporates a liquid nitrogen heat exchanger 89 as a backup. This has the capacity to maintain normal store conditions for a specified length of time, subject to availability of liquid nitrogen.

In an alternative embodiment (not shown) liquid nitrogen is used to cool the modules 90 whilst mechanical cooling is used for the corridor 35. Liquid nitrogen cooling systems are more reliable and easier to maintain than the cascade mechanical refrigeration systems mentioned above. There are also other significant advantages including the reduction in the cost of building services required to support the store.

The modules 90 are the most difficult parts of the store to service because of the very low temperature and the risk of samples experiencing transient warming effects and being exposed to moisture (icing). In order to improve reliability the number of serviceable items within the modules 90 has been kept to the minimum possible and moving parts and cabling within the modules 90 has been eliminated.

Most conventional freezer rooms use forced convection. Fans are mounted on evaporator coils, much in the same way as a car radiator, and the air to be chilled is forced through the matrix of cooling plates. This method has two advantages: namely efficient heat transfer resulting from the turbulent airflow over the cooling plates and uniformity of temperature distribution as a result of the forced circulation of air around the module 90. However, fans introduce an additional heat load into the modules 90 significantly increasing running costs. Furthermore, fans are not designed to operate in such low temperatures. Although, fan motors could be mounted externally and the fans driven by a shaft through the insulation, this adds complexity and would still require maintenance.

Figure 11:
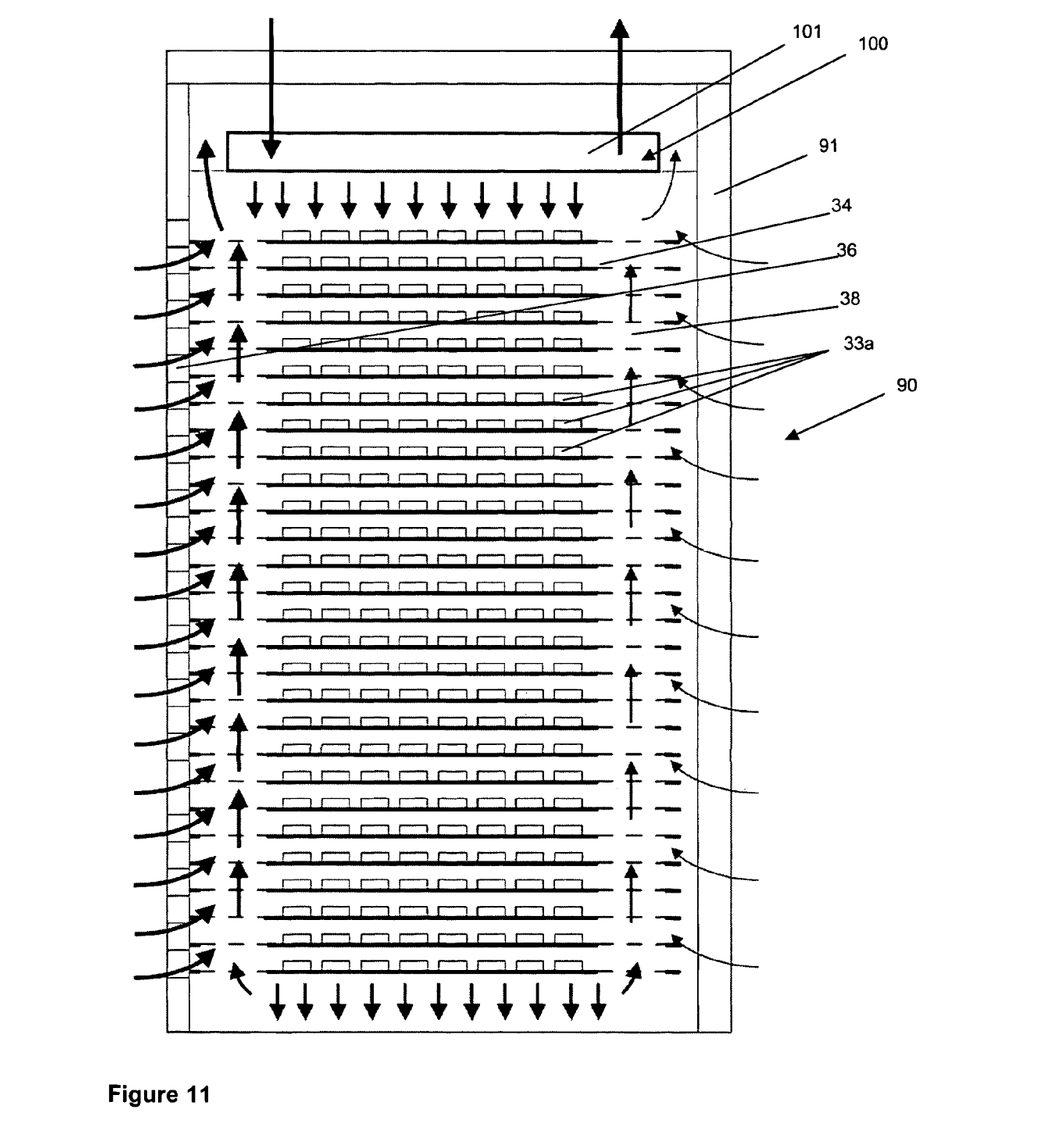
FIG. 11 shows a cross sectional schematic through a module.

FIG. 11 shows a nitrogen based cooling system 100 employed within each module 90. The walls 91 of the module 90 provide insulation. The system 100 consists of a large high integrity 9 way, 8 pass liquid nitrogen evaporator 101 into which nitrogen is injected, in use. The evaporator 101 is mounted above the storage locations 30. The footprint of the evaporator 101 is the same as that of the storage racking 29 and the contents of the sample vessels 33 are cooled by the cold air that falls though the evaporator fins (not shown). Warm air is returned to the evaporator through the chimneys 38 in the drawers 34.

A solenoid valve mounted on the outside of the module 90 in the −20° C. enclosure 20, for ease of maintenance, is used to regulate the flow of liquid nitrogen into the evaporator 101 and the waste gas is vented to the outdoors, no nitrogen is released into the module 90. The temperature within the module 90 is monitored by a plurality of thermocouples placed at the extremities of the module 90 to record the extremes of temperature within the module 90 and thereby monitor the temperature profile throughout the areas in which samples are stored.

The evaporator 101 is connected to flexible vacuum isolated pipework by compression fittings and can be pulled forwards through an access hatch into the aisle for de-icing purposes. It is also possible to disconnect the evaporator and replace it in the unlikely event of failure.

The invention claimed is:

1. A system for storing and processing a plurality of biological or chemical samples at ultra-low temperatures, the system comprising:
   a plurality of ultra-low temperature storage locations;
   an enclosed pathway adjacent the storage locations;
   a manipulator module disposed within the pathway for conveying vessels along the pathway between the storage locations in the system; and characterized by
   each of the storage locations being accessed through an insulated access panel on the side of the storage location, the panel being configured to close the storage location from the pathway.

2. The system according to claim 1, wherein the temperature of the pathway is maintained between ultra-low temperatures and the external environment.

3. The system according to claim 1, wherein the storage locations are maintained at approximately −80° C.

4. The system according to claim 1, wherein the temperature of the pathway is approximately −20° C.

5. The system according to claim 1, further comprising at least one module for housing the storage locations.

6. An enclosure for storing and processing a plurality of biological or chemical samples at ultra-low temperatures, the enclosure comprising:
   walls to close the enclosure;
   a plurality of modules defined by walls wherein each module comprises a plurality of compartments and is maintained, in use, at about −80° C.;
   a pathway maintained, in use, at about −20° C. and situated adjacent the modules;
   wherein walls of the enclosure are separated from the walls of the modules.

7. The enclosure according to claim 6, further comprising a manipulator module disposed within the pathway for conveying vessels along the pathway between the storage locations in the system.

8. The enclosure according to claim 6, wherein the compartments filled, in use, by drawers with integral access panels.

9. The enclosure to claim 6, wherein the compartments are filled, in use, by trays closed by separate access panels.

10. The system according to claim 1, wherein the access panel is pivotable, removable or slidable to enable the manipulator module to access the storage locations horizontally.

11. The system according to claim 5, wherein the modules are maintained at a maximum dewpoint of −40° C.

12. The system according to claim 1, wherein the manipulator module has an insulated surround in which samples can be maintained at ultra-low temperatures.

13. The system according to claim 1, further comprising a picker mounted with the manipulator module.

14. The system according to claim 1, wherein pathway includes an area in which the manipulator module can be "parked".

15. The enclosure according to claim 9, wherein the access panel is pivotable, removable or slidable to enable the manipulator module to access the storage locations horizontally.

16. The enclosure according to claim 9, wherein the modules are maintained at a maximum dewpoint of −40° C.

17. The enclosure according to claim 6, wherein the manipulator module has an insulated surround in which samples can be maintained at ultra-low temperatures.

18. The enclosure according to claim 6, further comprising a picker mounted with the manipulator module.

19. The enclosure according to claim 6, wherein pathway includes an area in which the manipulator module can be "parked".

* * * * *